US00PP08500P

United States Patent [19]

Smith

[11] Patent Number: Plant 8,500

[45] Date of Patent: Dec. 14, 1993

[54] DOGWOOD TREE "SPRING GROVE"

[75] Inventor: Thomas L. Smith, Cincinnati, Ohio

[73] Assignee: Spring Grove Cemetery and Arboretum, Cincinnati, Ohio

[21] Appl. No.: 773,137

[22] Filed: Oct. 8, 1991

[51] Int. Cl.[5] ..... A01H 5/00

[52] U.S. Cl. ..... Plt./53.2

[58] Field of Search ..... Plt./53.2

*Primary Examiner*—James R. Feyrer

*Assistant Examiner*—Erich E. Veitenheimer

*Attorney, Agent, or Firm*—Frost & Jacobs

[57] ABSTRACT

A white flowering dogwood tree showing better than usual cold and heat tolerance as well as bearing abundant multiple terminal floral bracts. This dogwood produces an unusual abundance of flowers as well as fruit, and exhibits a more pronounced broader than tall habit. There has been no appearance of anthracnose on this distinct variety of *Cornus florida*.

2 Drawing Sheets

SUMMARY OF THE INVENTION

This invention relates to a new and distinct improved variety of white flowering dogwood tree, being particularly noted for its hardiness and extremely floriferous habit, while maintaining a vigorous growth rate as well as exhibiting a broader than tall habit (as illustrated in FIG. 1) more pronounced than that of other dogwoods of the florida species, and excellent observed resistance to Anthracnose disease. This dogwood variety has survived winter temperatures as low as −26° F. (−32° C.) with no apparent vegetative tissue or floral tissue damage.

This new variety is a chance seedling that was first discovered as a superior dogwood in the mid 1970's. The tree is located in Spring Grove Cemetery, in Cincinnati, Ohio, and is approximately 45 years old. I have caused the tree to be asexually propagated by softwood cuttings, by budding, and by grafting and found that the distinctive characteristics hereof are retained. The budding was conducted in Winchester, Tenn., with the assistance of Shadow Nursery, Inc. The grafting was conducted in Perry, Ohio, with the assistance of the Herman Losley and Son Nursery, Inc.

Some of the important improvements provided by this variety are its extremely floriferous habit, with terminal branches frequently bearing 2 or 3 floral buds (as seen in FIG. 2) compared to the floral bud production of 'Cherokee Princess' which will typically bear one floral bud per Terminal Shoot. The *Cornus florida* selection 'Cloudnine' may bear more terminal buds than 'Spring Grove', however, 'Spring Grove' is a more vigorous grower than 'Cloudnine'. The floral bracts of *Cornus florida* 'Spring Grove' are white, and average about 5 inches (12.7 cm) from tip to tip which is comparable to that of 'Cherokee Princess'. The flowers are subtended by pedicels which average about 1.5 inches (3.8 cm) in length that hold the floral parts well above the foliage.

This Dogwood variety has weathered temperatures as low as −26° F. (−32° C.) with absolutely no floral or vegetative bud damage, while *Cornus florida* 'Springtime' and 'Cherokee Princess' received significant floral and vegetative damage, as did virtually all other florida selections within our collection.

The extremely floriferous habit relates directly to the abundant fruit set of this selection. Over years of close observation, we have seen no appearance or other signs of Anthracnose disease. Since 'Spring Grove' will produce 2 or 3 floral buds per terminal branch, the resulting quantity of fruit is greater than other *Cornus florida* cultivars such as 'Springtime' or 'Mystery'.

'Spring Grove' will generally exhibit full flowering at the same time as 'Cloudnine'. In Cincinnati, Ohio that would generally be approximately the last week of April. 'Spring Grove' currently has a height of 22 (6.6 m) feet and an average of crown spread of about 32 feet (9.75 m). The trunk is approximately 11½" (29.2 cm) in diameter measured at 3 feet (76.2 m) above ground level.

As a young budded tree (2 year bud graft), 'Spring Grove' has proven to be as vigorous as 'Cherokee Princess' under good growing conditions. The lenticels on 'Spring Grove' are less conspicuous than those of *Cornus florida* 'Cloudnine'. The Summer and Fall foliage color of 'Spring Grove' are not noticeably different than other non-variegated *Cornus florida* cultivars.

The stem color of the first and second years growth of 'Spring Grove' is somewhat variable. While some branches may exhibit a burgundy coloring, others may exhibit an olive green, as compared to *Cornus florida* 'Cloudnine' which exhibits a stem which is consistently burgundy colored on the upper on the upper surface and a downy green on the lower surface. Any apparent fragrance on our 'Spring Grove' selection is minimal. The seeds of 'Spring Grove' are viable and have been germinated at Spring Grove Cemetery in Cincinnati, Ohio.

BRIEF DESCRIPTION OF THE PHOTOGRAPHS

The color photographs accompanying this description, while subject to variations which are not able to be controlled, are as nearly representative of the color disclosures as is possible to make by this process. They are intended to show typical specimens of the vegetative growth and flowers of this new variety and its distinguishing combination of characteristics. The photographs are referred to by the following figure numbers:

DETAILED DESCRIPTION

The specimen described herein is being grown under cultivated conditions in Hamilton County, Ohio at Spring Grove Cemetery and Arboretum.

Parentage: Discovered seedling of *Cornus florida.*

Figure 1:
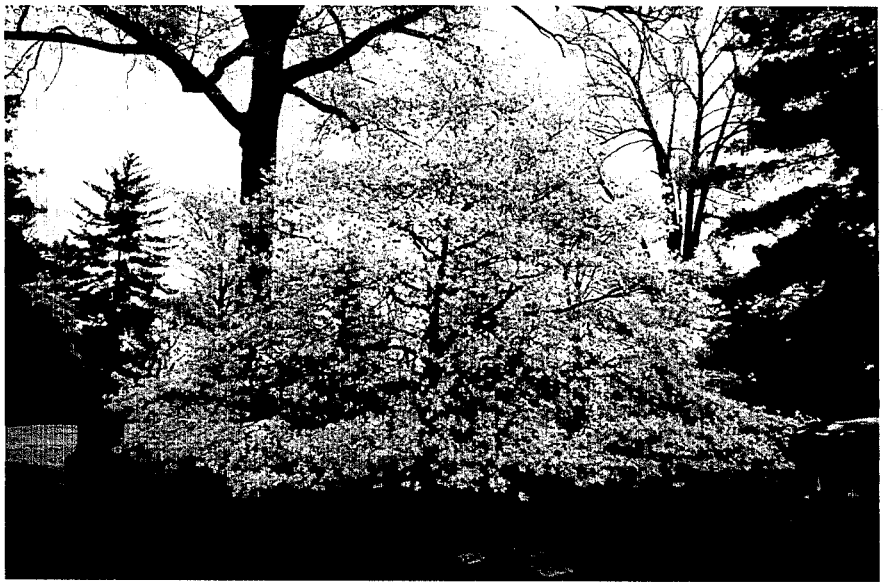
FIG. 1 shows typical overall shape and habit of the subject dogwood tree "Spring Grove"
Figure 4:
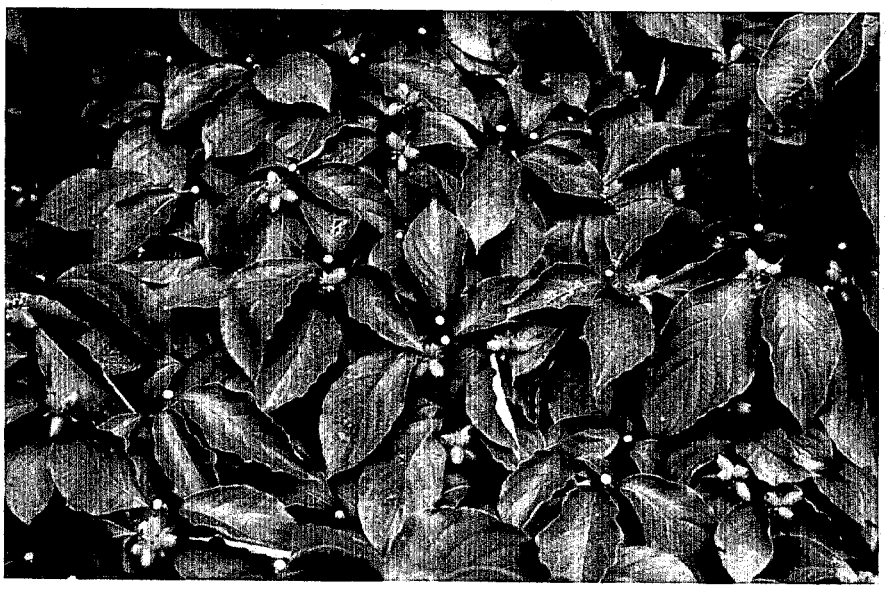
FIG. 4 shows typical abundant fruit production.

Tree: Medium; upright and spreading; vigorous, broader than tall; horizontal branching habit; rounded; hardy; extremely floriferous, large floral bracts; and abundant fruit set. Illustrated in FIGS. 1 and 4.

Trunk: Medium texture, becomes scaly with age.

Branches: Young stems are smooth and purplish, changing to green.

Leaves: Illustrated in FIG. 4.

*Length.*—Average 9.5–14.5 cm.

*Shape.*—Oval to ovate.

*Petiole.*—1.5–2.25 cm.

*Margin.*—Slightly crenate to entire, slightly undulated.

*Color.*—Summer leaves, Emerald Green (Royal Horticulture Colour Chart, page 99, Spectrum range position 758), Mature fall leaf color, Turkey Red (Royal Horticulture Colour Chart page 94, Spectrum range position 721/1).

Flower buds: Hardy to Zone 5, believed hardy to Zone 4.

*Size.*—Normal, 0.5 to 0.75 cm.

*Quantity.*—Frequently 2 or 3 terminal floral buds per terminal branch.

*Shape.*—Globose.

*Color.*—Grayish Green.

Figure 2:
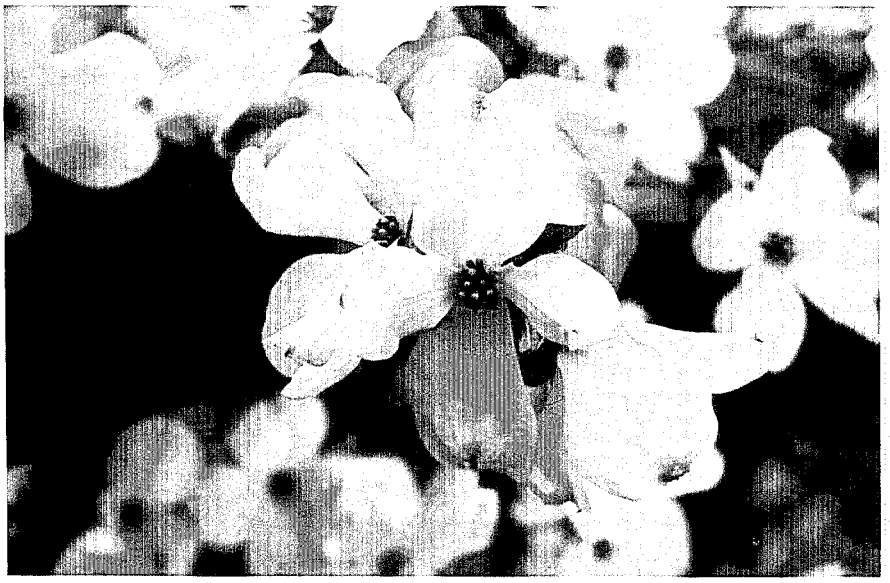
FIG. 2 shows typical abundance of floral parts.

Flowers: Illustrated in FIG. 2.

*Date of first bloom.*—generally April 17–22.

*Date of full bloom.*—generally April 24–May 2.

*Quantity.*—Abundant.

*Size.*—0.5 cm wide.

*Color.*—Greenish-yellow.

Figure 3:
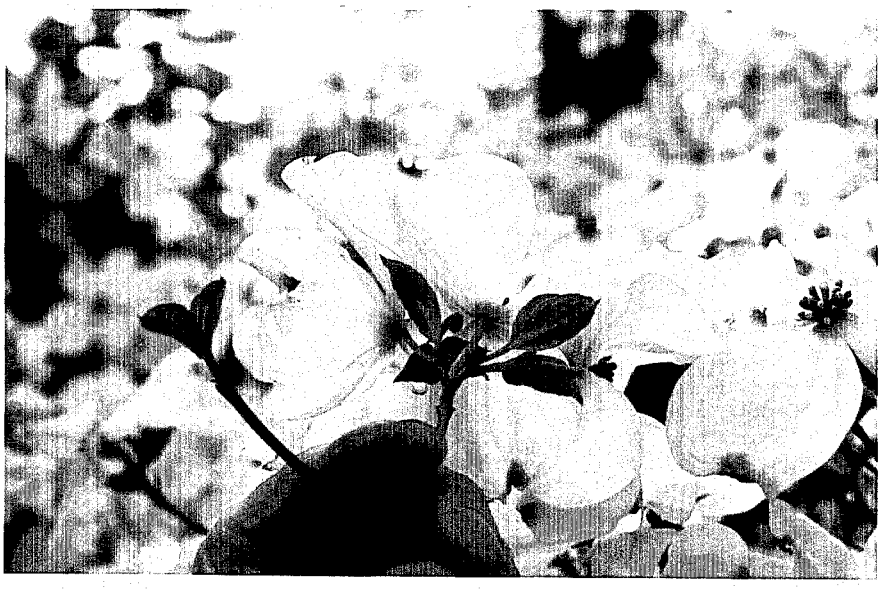
FIG. 3 shows typical multiple terminal floral structures.

Petalage:

*Petal-like bracts.*—Illustrated in FIG. 3.

*Number.*—4 petal-like bracts per floral inflorescence.

*Bud shape.*—Globose.

*Size.*—Large, 5.5–7 cm long; 5–7.5 cm wide.

*Color.*—White with notched bract tips Geranium Lake (Royal Horticulture Colour Chart page 20, Spectrum range position 20/2).

*Shape of bracts.*—Obovate; notched.

Fruit: Illustrated in FIG. 4.

*When borne.*—Summer.

*Abundance.*—Above average.

*Size.*—0.5 to 1 cm.

*Color.*—Mature fruit, Vermilion (Royal Horticulture Colour Chart page 18, Spectrum range position 18).

*Shape.*—Ovoid.

I claim:

1. A new and distinct variety of Dogwood tree, substantially as herein shown and described, characterized particularly as to novelty by the combination of its hardiness and extremely floriferous habit, vigorous growth rate, pronounced broader than tall habit, and resistance to Anthracnose disease.

* * * * *